US012275012B2

(12) United States Patent
Gavin et al.

(10) Patent No.: US 12,275,012 B2
(45) Date of Patent: Apr. 15, 2025

(54) METHOD OF PRODUCING A REAGENT TAPE, REAGENT TAPE AND MILKING DEVICE WITH A MILK SAMPLING DEVICE THEREWITH

(71) Applicant: LELY PATENT N.V., Maassluis (NL)

(72) Inventors: Peter Michael Gavin, Maassluis (NL); Darby Anne McChesney, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 963 days.

(21) Appl. No.: 17/273,765

(22) PCT Filed: Aug. 13, 2019

(86) PCT No.: PCT/NL2019/050527
§ 371 (c)(1),
(2) Date: Mar. 5, 2021

(87) PCT Pub. No.: WO2020/067876
PCT Pub. Date: Apr. 2, 2020

(65) Prior Publication Data
US 2021/0308683 A1 Oct. 7, 2021

Related U.S. Application Data

(60) Provisional application No. 62/735,212, filed on Sep. 24, 2018.

(51) Int. Cl.
*A01J 5/013* (2006.01)
*B01L 3/00* (2006.01)
(Continued)

(52) U.S. Cl.
CPC ............. *B01L 3/527* (2013.01); *A01J 5/0131* (2013.01); *G01N 1/10* (2013.01); *G01N 33/04* (2013.01);
(Continued)

(58) Field of Classification Search
CPC ................. B01L 3/527; B01L 2200/12; B01L 2300/0825; B01L 2300/165;
(Continued)

(56) References Cited

U.S. PATENT DOCUMENTS 7,524,456 B1\* 4/2009 Buechler ............... B01L 3/5027
422/412
8,129,195 B2 3/2012 Roeper et al.
(Continued)

FOREIGN PATENT DOCUMENTS

CN 1688882 A \* 10/2005 ............ B01L 3/5023
CN 101448392 A 6/2009
(Continued)

OTHER PUBLICATIONS

International Search Report, issued in PCT/NL2019/050527, dated Oct. 25, 2019.
(Continued)

*Primary Examiner* — Robert R Raevis
(74) *Attorney, Agent, or Firm* — Birch, Stewart, Kolasch & Birch, LLP

(57) ABSTRACT

A method of producing a reagent tape, that includes a base tape layer and a series of consecutive and separate reagent pads of a reagent, is provided for use in a milk sampling device. The milk sampling device is arranged to supply a droplet of a milk sample onto one of the reagent pads on the tape in order to produce a response in the reagent to detect a presence or concentration of a substance in the milk sample. The method includes providing the base tape layer of the reagent tape, applying onto the base tape layer a continuous layer of the reagent, dividing the supplied continuous reagent layer into separate reagent pads by providing a hydrophobic barrier line between said pads. This may be done by laser ablating thin lines of reagent material, or by (Continued)

Figure 1:
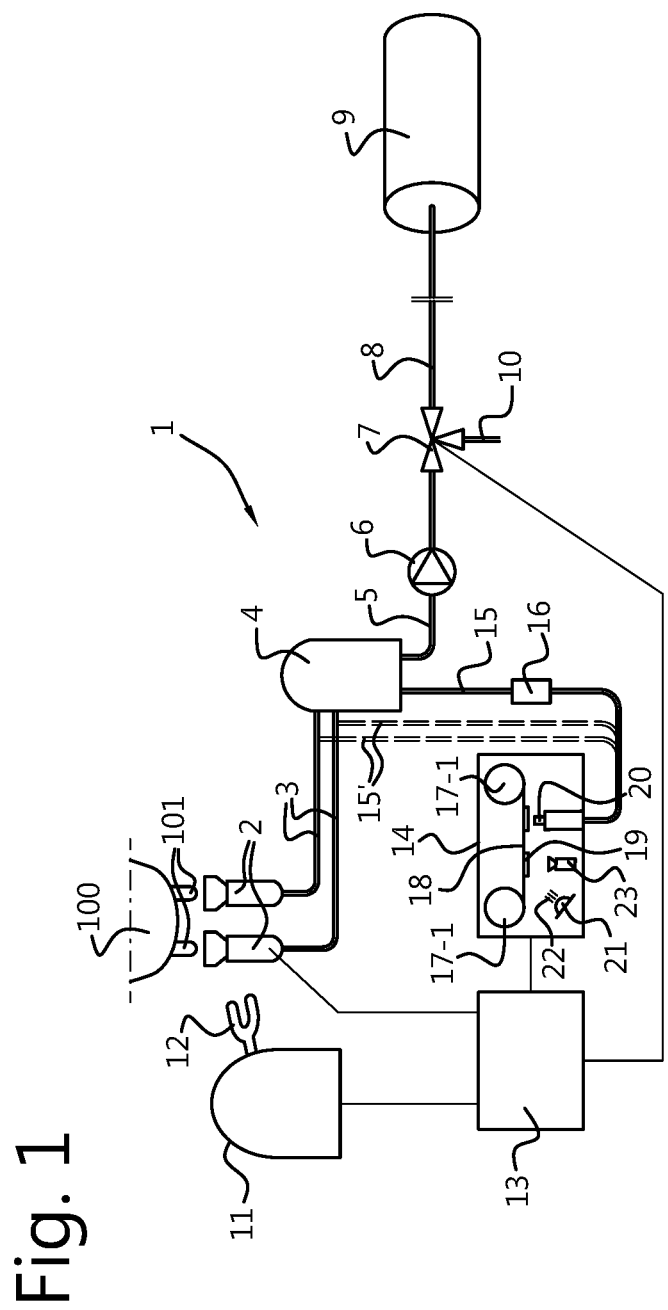

providing additional hydrophobic material into the layer. Thus, a simple and fast way of providing a tape with pads is obtained, in which a narrow spacing between pads is possible. A tape made by the method, and a milking device with a sampling device with such a tape are disclosed.

10 Claims, 2 Drawing Sheets

(51) Int. Cl.
    *G01N 1/10*      (2006.01)
    *G01N 33/04*      (2006.01)
    *G01N 35/00*      (2006.01)

(52) U.S. Cl.
    CPC . *G01N 35/00009* (2013.01); *G01N 35/00029* (2013.01); *B01L 2200/12* (2013.01); *B01L 2300/0825* (2013.01); *B01L 2300/165* (2013.01); *G01N 2035/00039* (2013.01); *G01N 2035/00118* (2013.01)

(58) Field of Classification Search
    CPC . B01L 2300/161; A01J 5/0131; A01J 5/0435; G01N 1/10; G01N 33/04; G01N 35/00009; G01N 35/00029; G01N 2035/00039; G01N 2035/00118; G01N 21/8483
    USPC ........... 73/53.01, 53.02, 61.41, 61.43, 61.44, 73/61.48, 61.59, 64.56, 863, 863.31, 73/863.81, 863.83, 864, 864.34, 864.73, 73/864.81; 422/74, 83.05; 119/14.14, 119/14.27
    See application file for complete search history.

(56) References Cited

U.S. PATENT DOCUMENTS

| | | |
|---|---|---|
| 2009/0078206 A1 | 3/2009 | Watanabe |
| 2009/0255473 A1 | 10/2009 | Katz et al. |
| 2012/0045825 A1 | 2/2012 | Harttig et al. |
| 2017/0027128 A1 | 2/2017 | Van Tilburg et al. |
| 2017/0099801 A1 | 4/2017 | Van Tilburg et al. |

FOREIGN PATENT DOCUMENTS

| | | | |
|---|---|---|---|
| CN | 102084247 A | 6/2011 | |
| CN | 104704363 A | 6/2015 | |
| CN | 106455515 A | 2/2017 | |
| CN | 106455517 A | 2/2017 | |
| EP | 1 381 269 B1 | 10/2004 | |
| WO | WO-2014012558 A2 * | 1/2014 | ............ A01J 5/0131 |

OTHER PUBLICATIONS

Written Opinion of the International Searching Authority, issued in PCT/NL2019/050527, dated Oct. 25, 2019.

\* cited by examiner

METHOD OF PRODUCING A REAGENT TAPE, REAGENT TAPE AND MILKING DEVICE WITH A MILK SAMPLING DEVICE THEREWITH

CROSS REFERENCE TO RELATED APPLICATIONS

This application is the National Phase of PCT International Application No. PCT/NL2019/050527, filed on Aug. 13, 2019, which claims priority under 35 U.S.C. 119 (e) to U.S. Provisional Application No. 62/735,212, filed on Sep. 24, 2018, all of which are hereby expressly incorporated by reference into the present application.

The present invention relates to a method of producing a reagent tape, that comprises a base tape layer and a series of consecutive and separate reagent pads of a reagent, for use in a milk sampling device, the milk sampling device being arranged to supply a droplet of a milk sample onto one of the reagent pads on the tape in order to produce a response in the reagent to detect a presence or concentration of a substance in the milk sample.

Document EP1381269 discloses a system for optimising the production performance of a milk producing animal herd, in which chemical analysis means are used which comprise a carrier tape onto which a series of separate and consecutive test strips or dry sticks are arranged, with flush holes inbetween. However, no details of a way to produce same are disclosed.

It is an object of the present invention to provide a method of producing such a reagent tape in a simple, fast and economical way.

The present invention achieves the above object at least partly by means of a method according to claim 1, in particular a method of producing a reagent tape, that comprises a base tape layer and a series of consecutive and separate reagent pads of a reagent, for use in a milk sampling device, the milk sampling device being arranged to supply a droplet of a milk sample onto one of the reagent pads on the tape in order to produce a response in the reagent to detect a presence or concentration of a substance in the milk sample, the method comprising providing the base tape layer of the reagent tape, applying onto the base tape layer a continuous layer of the reagent, dividing the supplied continuous reagent layer into separate reagent pads by providing a hydrophobic barrier line between said pads.

According to the present invention, there is no need to prepare separate test strips or dry sticks, and apply these to a carrier tape. Rather, the reagent pads are applied in one single step, which is very simple and quick to achieve, while the separating step is performed by means of providing a hydrophobic barrier line between the pads. This line prevents that liquid jumps over between neighbouring pads. Thereto, a number of options are available, as will be shown below. Herein, it is advantageous that the reagent is applied as a continuous layer, so that its properties, and in particular its thickness, is controllable within tight margins.

In addition, the hydrophobic barrier line can be made extremely narrow, and thus provide the possibility to obtain reagent pads at a very small mutual distance, that still act as separate pads. This contrasts with a much larger distance that would be required when arranging test strips or dry sticks onto a carrier tape, due to movement and mechanical tolerances. An advantage of this possible very close distance is that the same carrier tape can now carry more pads, such that it will be less often necessary to replace a carrier tape. This is advantageous in automated sampling systems, that do not need human supervision. By having more reagent pads per tape, such a system may work for a longer time without human intervention. Moreover, because of the easy control of a line supply device or a laser ablation beam, it would also be more easily possible to change the settings on the fly even during production of the tape, or to apply different settings on purpose, such as for alternating tests on the tape that require a different reagent area or the like. This increased variability is also an advantage of the present invention.

The production of the tape in all is thus flexible, easy and economical and very fast.

Here it is noted that it is not an obvious step to produce a tape with reagent pads that are so close to each other, at least in desired cases. After all, to ensure that a sample drop can react with the reagent in the pad, the pad should absorb the liquid rather quickly, and the pad will then quickly spread the liquid to the very borders of the pad. When the next pad is very close, chances are that the liquid will spread to the next, neighbouring pad. However, the inventors have found that even at very close range, liquid will not cross the hydrophobic barrier line to the neighbouring pad.

Particular embodiments and advantages are described in the dependent claims, as well in the now following part of the description.

In embodiments, the step of providing a hydrophobic barrier line comprises removing at least a, preferably throughgoing, strip of reagent in a direction transverse to a longitudinal direction of the tape by means of laser ablating. The latter is a very simple and fast step, since a laser beam is easily controlled, such as to the depth of removing material. It is easily possible to set the laser beam such that it removes just all the reagent material in the strip, that is, right down to the base tape layer. Note that it is not always necessary to remove a throughgoing strip of material, if the remaining (reagent) material no longer allows liquid to pass from pad to pad, for example because the remaining material was also altered by the laser beam, such as being burnt or molten liquid-impervious by the laser beam. The mechanism is not yet understood. It could for example be caused by the strip of removed material being, though very narrow, still wider than the required width for capillary action. Alternatively, it could be that the laser beam changes the properties of the material, such that it now repels liquid, or that it even melts close the capillaries near the ablation line. In any case, it was found that even at a small width of, say, a tenth of a millimeter, liquid would not pass from pad to pad. Based on the eventual understanding of the mechanism, it may prove possible to find alternative methods for producing a tape with such reagent pads at close mutual distances. For example, if the key in these embodiments is simply to remove a strip of reagent material, it might suffice to mechanically remove the strip of material, such as by grinding, or by etching, although these methods would probably prove more cumbersome. If the key would be to alter the properties of the material, the use of chemicals, or spot-welding or the like, might also work, although these methods would, again, probably be much more cumbersome than using a laser beam for ablating the material.

In embodiments, said laser ablating comprises removing between two neighbouring reagent pads two mutually parallel, and preferably throughgoing, strips of the reagent. With this measure, there is now a double barrier between the pads, which even further improves their mutual independence, be it at the cost of the distance between two pads. Still, the production speed and flexibility are improved with respect to known tape production methods. An additional advantage of having a wider distance between two pads is that, when a tape is stored in a cassette that protects unused reagent pads against the environment, such as humidity, dust and light, it is then easier to seal of the unused parts of the tape by means of e.g. a duckbill valve or other means on the cassette. If the pads would be separated by just the strip with a width of the very narrow laser ablation beam, it could be possible for liquid to travel between pads via the sealing surface of the duckbill valve or the like. Alternatively, the duckbill valve or the like would have to have a sealing surface that is at most as wide as the removed strip, which is not only not very realistic, but also prone to wear and tear. Note also that it is alternatively possible to laser ablate just one, but a wider strip of material, such as with a width of not a tenth of a millimeter but, say, one millimeter. Although this will take longer in most case, it may provide better sealing capabilities due to the absence of reagent material between the reagent pads, and thus a lower local thickness.

In embodiments, the step of providing a hydrophobic barrier line comprises applying a line of hydrophobic material onto and into the reagent layer. Such a line also creates separate pads out of the single continuous layer of reagent material. The hydrophobic nature of the material used for the line ensures that liquid will not pass from one reagent pad to the next. Note that in all of the present invention it is understood that the liquid is a watery liquid, such as in particular milk or blood. Liquids that would not be repelled by the hydrophobic material of the lines, such as possibly molten fats or the like, are expressly excluded.

The hydrophobic material may be a (liquid or liquified) polymer with hydrophobic properties, such as a teflon or teflon-based polymer. Since the hydrophobic material should also prevent the liquid from flowing to a neighbouring pad underneath the line, the material should penetrate into the reagent material to block liquid-flow there as well. The selection of a suitable hydrophobic material thus also depends on the properties of the reagent material, but is readily made in practice. The material may be provided by means of a printer-like device, or simply a nozzle, either line-shaped, movable across the tape or a series of nozzles. The linewidth may be as narrow as one or a few tenths of a millimeter, but may alternatively be made sufficiently wide for sealing by means of a sealing element, cfr. the double laser ablation line described above.

In embodiments, the step of applying reagent comprises applying a plurality of mutually parallel continuous track-like layers of a respective reagent onto the base tape layer. The advantages for a single track of reagent material that is formed into separate pads applies equally well to two or more of such tracks of, preferably, different reagent materials. This allows to produce a tape with a variety of reagent materials easily, quickly and economically. Note that it is not necessary that the pads are all of the same size. For example, it is possible to provide reagent pads for a first reagent material with a first length (i.e. distance between the two limiting strips), while pads of a second reagent material may be given a different second length. This, too, is due to the fact that a laser beam is very easily controlled, and may even be controlled between different tracks of reagent material. of course, in case all pads are given the same length, it is easy to guide the laser ablation beam across all of the tape in one go, possibly switching off the beam when it is above the part of the tape between the different tracks of reagent materials. In all of this, it is possible to apply the various reagent material consecutively or, preferably, simultaneously.

In embodiments, the reagent material and the base tape layer are each provided wound onto a bobbin or the like, wherein the method comprises uniting the reagent material and the base tape layer by simultaneously unwinding the respective bobbins and bringing the reagent material onto the base tape layer. Depending on the properties of the reagent material and/or the base tape layer, it may be advantageous to supply an additional layer for uniting the reagent material and the base tape layer. For example, there may be provided an adhesive layer onto the base tape layer, onto the reagent material or even as a separate material also wound on a bobbin or the like and, in any case, provided between the reagent material and the base tape layer.

In attractive embodiments, the step of applying reagent material comprises providing an application nozzle for supplying the, or each respective, reagent material, and moving the base tape layer passed the, or each, nozzle, to thereby apply the, or each, reagent material as a continuous layer onto the tape. Herein, the, or each, reagent material is supplied from a supply container, through a nozzle, onto the base tape. The reagent material will then be either a fluid itself, or combined with one or more other materials such that the result is an applicable fluid. In all cases, a subsequent step, such as a curing step by means of UV light or the like, to stabilise the reagent material may be applied when needed. Note that it is also possible to supply one or more reagent materials as or in a fluid, and to supply one or more reagent materials from a respective bobbin or the like, i.e. as a solid, tape-like material.

The invention also relates to a reagent tape, that comprises a base tape layer and a series of consecutive and separate reagent pads of a reagent, the tape being produced with a method according to the present invention. Such a tape will have at least some of the advantages described above for the method. In addition, it is to be remarked that in use of the tape, the average centre-to-centre distance of the pads can be made smaller than in existing reagent tapes. This makes it possible to move the tape quicker. In particular shifting the reagent tape according to the invention over one reagent pad length takes less time than similarly moving a known tape, in each case with the same speed. Thus, either a higher throughput or a similar throughput with lower speed and thus lower forces is achievable according to the invention.

The invention also relates to a milking device with a milk sampling device, the milking device arranged to draw milk from a dairy animal, wherein the milk sampling device comprises an analyser with a reagent tape according to the invention, and a sampler supply a milk sample from the milk drawn from the dairy animal to a reagent pad of the reagent tape, the analyser being arranged to analyse said at least part of the milk sample for the presence of at least one substance by observing a change in said reagent pad. As indicated above, the present invention offers the advantage that more reagent pads may be provided on a tape, and thus the milk sampling device may work for a longer period without human intervention, in particular for chaning the tape. This advantage is particularly useful for milking stalls in which the dairy animals walk about freely and in which the milking device is a robotic milking device with one or more milking robots. In such milking stalls, it cannot be predicted when the next animal will be milked, and thus neither when the next sampling is needed. Therefore, human operators or human intervention is minimal in such milking stalls, and thus the advantage of the milk sampling device being able to work for a prolonged period is important here.

Figure 2:
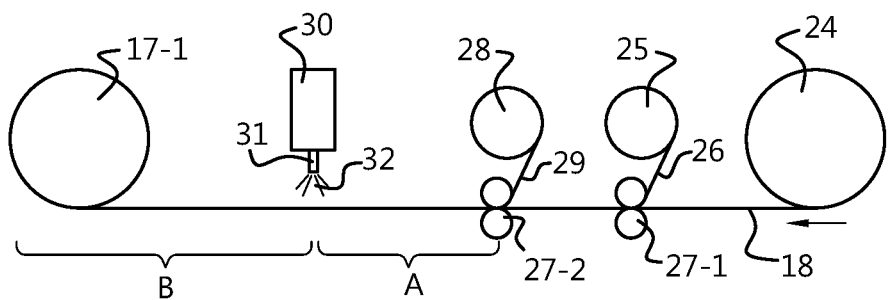
Figure 3:
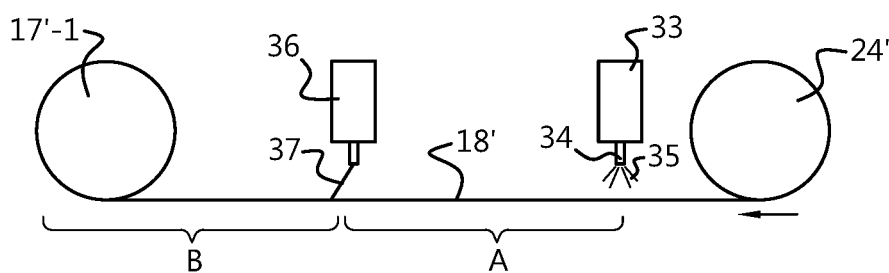
Figure 4:
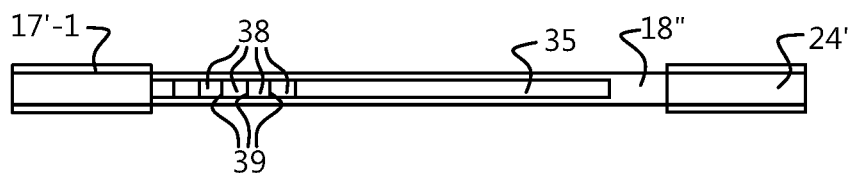
Figure 5:
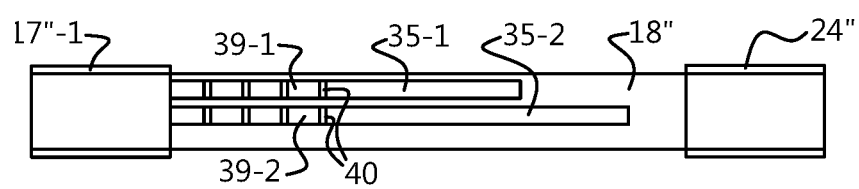
Figure 6:
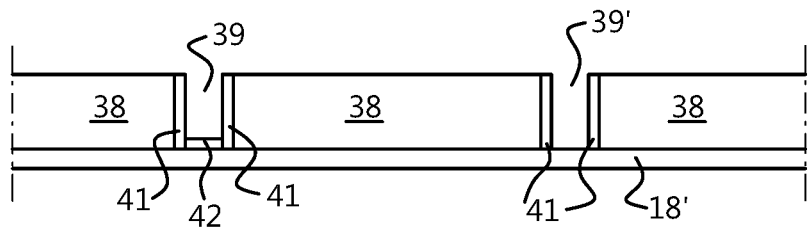
Figure 7:
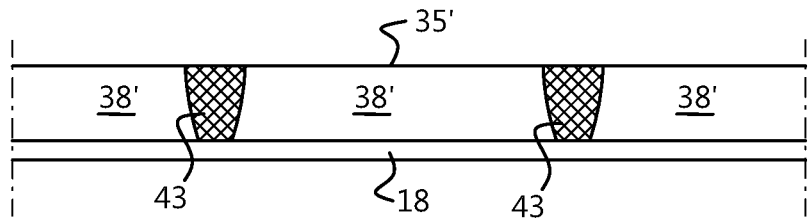

The invention will now be elucidated by way of a number of exemplary embodiments and the drawings, in which FIG. 1 shows a diagrammatic representation of a milking system according to the present invention;

FIGS. 2 and 3 diagrammatically show two embodiments of the method according to the present invention in a side view;

FIGS. 4 and 5 diagrammatically show in a top view two embodiments of the method according to the present invention; and FIGS. 6 and 7 diagrammatically show a detailed close-up view of a embodiments of a tape according to the present invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. The sampling unit 14 comprises a supply reel 17-1 and a collecting reel 17-2 for a tape 18 with reagent pads 19. A nozzle device for sample droplets is denoted by 20, a light source 21 emits light 22, and a camera is denoted by 23.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 15. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on.

A sampling unit 14 is very generally shown further, in that it here contains a supply reel 17-1 and a collecting reel 17-2, between which a tape 18 is wound down by means of non-shown tape mover means, such as a cassette deck motor or stepper motor. The tape 18 carries reagent pads 19 that contain reagent that gives a detectable response in the presence of a defined substance, often the intensity of the response depending on the concentration of the substance brought into the reagent via the sample droplet. Such a sample droplet is delivered via the nozzle 20. A light source 21 then shines light 22 onto the reagent pad 19, and a camera 23 observes the response, if any, in the reagent pad. The light source 21 may be any suitable light source, such as one or more LEDs, and the emitted light 22 may be visible light, UV(A) radiation, (near) infrared, and so on, depending on the used reagent. Of course, the camera 23 should be adapted to detect radiation coming from the reagent pad 19. Often, this is reflected or scattered light, but it could be different radiation, such as fluorescence radiation. In any case, details of such radiation and detection may easily be implemented by the skilled person and do not form the present invention as such.

It is remarked here that the camera 23 and the light source 21 are shown below the tape 18 with the reagent pads 19. In practice, it may also occur, and in fact often be advantageous, if the camera 23 and the light source 21 are positioned above the tape 18. This allows the camera to image the reagent pad to which the sample droplet is supplied without advancing the tape, i.e. immediately. In addition, there is no risk of any liquid, or dirt, falling from the reagent pad to the camera and/or light source. Moreover, in general, it is advantageous if the camera 23 and/or the light source 21 are positioned outside the sampling unit 14, or rather outside a housing of the sampling unit. The camera and the light source are still functional parts of the sampling unit as a whole, but the former two parts are positioned outside a housing with the tape (reels) and the supply nozzle 20.

FIGS. 2 and 3 diagrammatically show two embodiments of the method according to the present invention in a side view.

To begin with FIG. 2, it shows a first reel 24 with blank tape material 18, a second reel with adhesive material 26, and a third reel 28 with reagent material 29. Also shown are pressing rollers 27.

A reservoir 30 with a nozzle device 31 sprays hydrophobic barrier material 32. The final result is wound onto the supply reel 17-1, cfr. the supply reel in FIG. 1. With brackets A, and B, the part of the tape with a continuous layer of reagent, and the part with separate reagent pads, respectively, have been indicated.

The method shown here provides for making a tape with separate reagent pads in a simple, fast and reliable way. It starts with blank tape reel 24, from which blank tape material 18 is unrolled in a direction of the arrow shown. Then, in an optional step, adhesive material 26 is unrolled from a second reel 25, and guided to the blank tape material 18, after which they are pressed together with the help of, optionally heated, rollers 27-1. In a next step, reagent material 29 is unrolled from a third reel 28, and guided to the blank tape—adhesive combination, and these are pressed together by the, optionally heated, rollers 27-2. What is now obtained is a tape material 18 with a continuous layer of reagent 29 thereon, if desired with an adhesive layer 26 inbetween.

In a next step, a nozzle device 31 sprays hydrophobic barrier material 32, from a reservoir 30, onto the reagent layer 29, in the form of barrier lines. These barrier lines separate reagent pads from each other, because the (watery) sample liquids will not cross the hydrophobic barrier lines. Thus, in part B of the drawing, there are separate reagent pads, while in part A there is still a continuous layer of reagent 29. For the nozzle device 31, it may be advantageous to use a position controlled nozzle, a set of parallel nozzles or the like, such as those that are used in (inkjet) printers. However, any type suffices, as long as the nozzle device 31 is able to apply the material 32 in the form of a line or the like. The hydrophobic material 32 may also be selected from several known materials, such as paraffine or TFE polymers. The choice may depend on whether the reagent material 29 allows the hydrophobic material to penetrate down to the layer therebeneath (adhesive 26, if any, the blank tape material 18, or any other layer provided beneath the reagent layer 29).

FIG. 3 shows an advantageous alternative embodiment of the method, in which similar parts are denoted with hyphened reference numerals. Thus, a blank tape 18' is unrolled from a supply reel 24', in the direction of the arrow. A reservoir 33 holds reagent material 35 that is sprayed by nozzle 34. A laser device 36 emits a laser beam 37. the finished tape is rolled onto the reel 17'-1.

In this embodiment, the blank tape 18' is coated with a layer of reagent material 35 by spraying it onto the tape with a nozzle 34. Herein, the reagent material 35 is often a combination of a pure reagent, such as an enzyme, with some additive to make it sprayable, such as a solvent. Other methods of applying the reagent material 35 are also possible, such as a contact roller or the like, as long as a continuous layer is obtained.

Subsequently, the continuous layer of reagent material is divided into separate reagent pads by means of a controllable laser beam 37 from a laser device 36. The laser beam 37 removes a thin strip of reagent material from the tape 18', and thereby creates a laser ablation line, or alters the properties of at least a border region of the pads, all this such that a drop of sample liquid will not go from one reagent pad to a neighbouring pad. The finished tape is then rolled up onto the reel 17'-1. Again, the part of the tape with the continuous layer of reagent material is indicated with "A", and the part with the separate reagent pads is indicated with "B".

FIGS. 4 and 5 diagrammatically show in a top view two embodiments of the method according to the present invention. In particular, FIG. 4 shows a top view of the embodiment of FIG. 3. From the right, a blank tape 18' is unrolled from the reel 24', and is then provided with a continuous layer 35 of reagent material. Then the controllable laser beam provides laser ablation lines 39 to make separate reagent pads 38. These lines 39 can be made very narrow, down to about 0.1 mm if desired. this allows the reagent pads 38 to be very closely spaced, so that each tape 18' can have many, many pads. This in turn allows a prolonged use of one and the same tape 18'; without human intervention, such as for exchanging the tape.

FIG. 5 shows a top view of an alternative embodiment. Here, the 18" is wider, and has room for two parallel tracks of reagent materials 35-1 and 35-2, that are supplied to the tape consecutively, although it could be possible to provide them at the same time, i.e. in parallel. Note that the embodiment of FIG. 2 might serve to provide this method, when the material 26 would not be an adhesive below the reagent material, but would be another reagent material next to reagent material 29.

However provided, the reagent materials 35-1 and 35-2 are present as parallel, continuous tracks or layers. Again, these tracks are divided into separate pads 39-1 and 39-2, respectively, by means of a laser beam. Here, however, the beam does not provide single laser ablation lines between the pads, but pairs 40 of laser ablation lines. This not only further improves the liquid barrier properties between the consecutive pads, but also allows sealing with a sealing means onto the pads without forming a bridge for liquid between two pads. It is noted that this also means that the consecutive pads 39 are spaced less closely as a consequence of allowing sealing. Yet, the spacing may still be narrow, while the invention as a whole still allows extremely narrow spacing.

FIGS. 6 and 7 diagrammatically show a detailed close-up view of a embodiments of a tape according to the present invention. FIG. 6 diagrammatically shows a finished tape with the base tape layer 18', with reagent pads 38 on top, separated by laser ablation lines 39 and 39'. Also indicated are material layers 41 and 42.

The material layers 41 are believed to be present in some cases, although applicant does not wish to be tied to this or any other application. The laser beam, that is used to remove the reagent material in order to provide a laser ablation line 39 and form pads 38, heats up the reagent material and evaporates it. However, it could be that reagent material in the layer 41 next to the removed material is heated up only so far as to melt and seal itself. This then changes the properties of the reagent layer, since that should allow liquid to penetrate through the material, in order for a sample droplet to reach the true reagent (enzyme or the like) in the reagent material. It could be that the layer 41 actually becomes impervious to the liquid, to support the liquid barrier properties of the laser ablation line. The same (as yet untested) hypothesis holds for the layer 42 at the bottom of the laser ablation line 39. If indeed the properties are changed such that that layer 42 does not allow liquid to go through, it suffices for it to remain present at the bottom of the laser ablation line. In other words, it is then not necessary for the laser beam to remove any and all material down to the blank base tape material 18'. However, it is stressed here that this is just a theory to explain the observed phenomenon of liquid barrier properties of a laser ablation line between reagent pads 38.

To the right in the FIG. 6, there is shown another laser ablation line 39', in which all reagent material actually has been removed down to the blank base tape material layer 18'. It is clear that no liquid will go from one reagent pad 38 to a neighbouring pad.

FIG. 7 diagrammatically shows a detailed close-up view of a another embodiment of a tape according to the present invention. Here, there is no laser ablation line, but the liquid barrier line between neighbouring reagent pads 38 is now formed by means of applying a hydrophobic barrier material in a narrow zone 43, such as with the method described for FIG. 2. It can be seen that in principle there still a continuous layer 35' of reagent material. However, because a hydrophobic barrier material such as a teflon-like polymer has been applied onto and into that layer 35', in the form of a barrier line 43, still separate reagent pads 38' have been formed. It is possible that the zone or line 43 protrudes somewhat above the layer 35', which in fact might even help as an additional liquid barrier between the pads 38'.

The above described embodiments only serve to help explain the invention without limiting this in any way. The scope of the invention is rather determined by the appended claims.

The invention claimed is:

1. A method of producing a reagent tape, that comprises a base tape layer and a series of consecutive and separate reagent pads of a reagent, for use in a milk sampling device, the milk sampling device being arranged to supply a droplet of a milk sample onto one of the reagent pads on the tape in order to produce a response in the reagent to detect a presence or concentration of a substance in the milk sample, the method comprising:
   providing the base tape layer of the reagent tape;
   applying onto the base tape layer a continuous layer of the reagent; and
   dividing the supplied continuous reagent layer into separate reagent pads by providing a hydrophobic barrier line,
   wherein the step of providing a hydrophobic barrier line comprises removing two mutually parallel strips of reagent in a direction transverse to a longitudinal direction of the tape by laser ablating to form neighboring reagent pads.

2. The method according to claim 1, wherein the step of providing a hydrophobic barrier line comprises applying a line of hydrophobic material onto and into the reagent layer.

3. The method according to claim 2, wherein the step of applying reagent comprises applying a plurality of mutually parallel continuous track-like layers of a respective reagent onto the base tape layer.

4. The method according to claim 2, wherein the reagent material and the base tape layer are each provided wound onto a bobbin, wherein the applying onto the base tape layer a continuous layer of the reagent comprises simultaneously unwinding the respective bobbins and bringing the reagent material onto the base tape layer.

5. The method according to claim 1, wherein the step of applying reagent comprises applying a plurality of mutually parallel continuous track-like layers of a respective reagent onto the base tape layer.

6. The method according to claim 1, wherein the reagent material and the base tape layer are each provided wound onto a bobbin, wherein applying onto the base tape layer a continuous layer of the reagent comprises simultaneously unwinding the respective bobbins and bringing the reagent material onto the base tape layer.

7. The method according to claim 1, wherein the step of applying reagent material comprises providing an application nozzle for supplying the reagent material, and moving the base tape layer passed the nozzle, to thereby apply the, reagent material as a continuous layer onto the tape.

8. The method according to claim 1, wherein the step of removing two mutually parallel strips of the reagent to form neighboring reagent pads comprises removing at least a throughgoing strip of reagent in a direction transverse to a longitudinal direction of the tape by laser ablating.

9. The method according to claim 1, wherein said laser ablating further comprises removing two mutually parallel throughgoing strips of the reagent.

10. The method according to claim 1, wherein the step of applying reagent comprises simultaneously applying a plurality of mutually parallel continuous track-like layers of a respective reagent onto the base tape layer.

* * * * *